United States Patent [19]

Korduner et al.

[11] 4,312,856

[45] Jan. 26, 1982

[54] BEVERAGE PRODUCT

[75] Inventors: Hans M. Korduner, Stockholm; Hans E. Gyllang, Täby; Kjell Y. Ericson, Upplands-Väsby, all of Sweden

[73] Assignee: AB Pripps Bryggerier, Bromma, Sweden

[21] Appl. No.: 130,222

[22] Filed: Mar. 14, 1980

[30] Foreign Application Priority Data

Feb. 15, 1980 [SE] Sweden ............................... 8001244

[51] Int. Cl.$^3$ ..................... A61K 31/70; A61K 33/06; A61K 33/14; A61K 33/30
[52] U.S. Cl. ................................... 424/145; 424/153; 424/154; 424/180
[58] Field of Search ................ 424/153, 154, 180, 145

[56] References Cited

U.S. PATENT DOCUMENTS 4,201,772  5/1980  Ingelman et al. .................... 424/180

Primary Examiner—Stanley J. Friedman
Attorney, Agent, or Firm—Abelman, Frayne & Rezac

[57] ABSTRACT

Beverage product, especially for rapidly replacing liquid and carbohydrates in the human body during periods of heavy muscle work, consisting of an essentially monosaccharide-free, hypotonic solution of soluble oligosaccharides and/or polysaccharides and mineral salts such as sodium chloride and other salts occurring in body liquids in an amount of at the most 3 grams per liter beverage, preferably at the most 1.5 grams per liter, which solution may contain suspended particles of insoluble polysaccharides, optionally together with a minor amount of aroma substances conventionally used in such products, and vitamin additives. The solution or suspension has an osmotic pressure in the range of about 7.5-1.0 atmospheres at 25° C., preferably 6.0-2.5 atmospheres and especially 5.5-3.0 atmospheres. The beverage product contains as the oligosaccharide a from the taste point of view desirable amount of one or more sweetly tasting oligosaccharides within the DP range 2-5, such as saccharose and maltotriose, in combination with polysaccharides with an average molecular weight within the range from 900 up to the molecular weight of starch, preferably about 900-2500, in which case the product is essentially clearly water-soluble. Preferred embodiments are beverages containing 20-70 grams of saccharose, 5-200 grams of essentially water-soluble oligosaccharides with an average molecular weight in the range of about 900-2500, aroma substances and mineral salts in an amount of about 0.5-1.5 grams per liter beverage. A process for rapidly replacing water lost by perspiration and preventing a decrease of the glucose content of blood during periods of extended heavy muscle work is characterized by per os administrating a beverage product according to the definition above to the human body.

11 Claims, 3 Drawing Figures

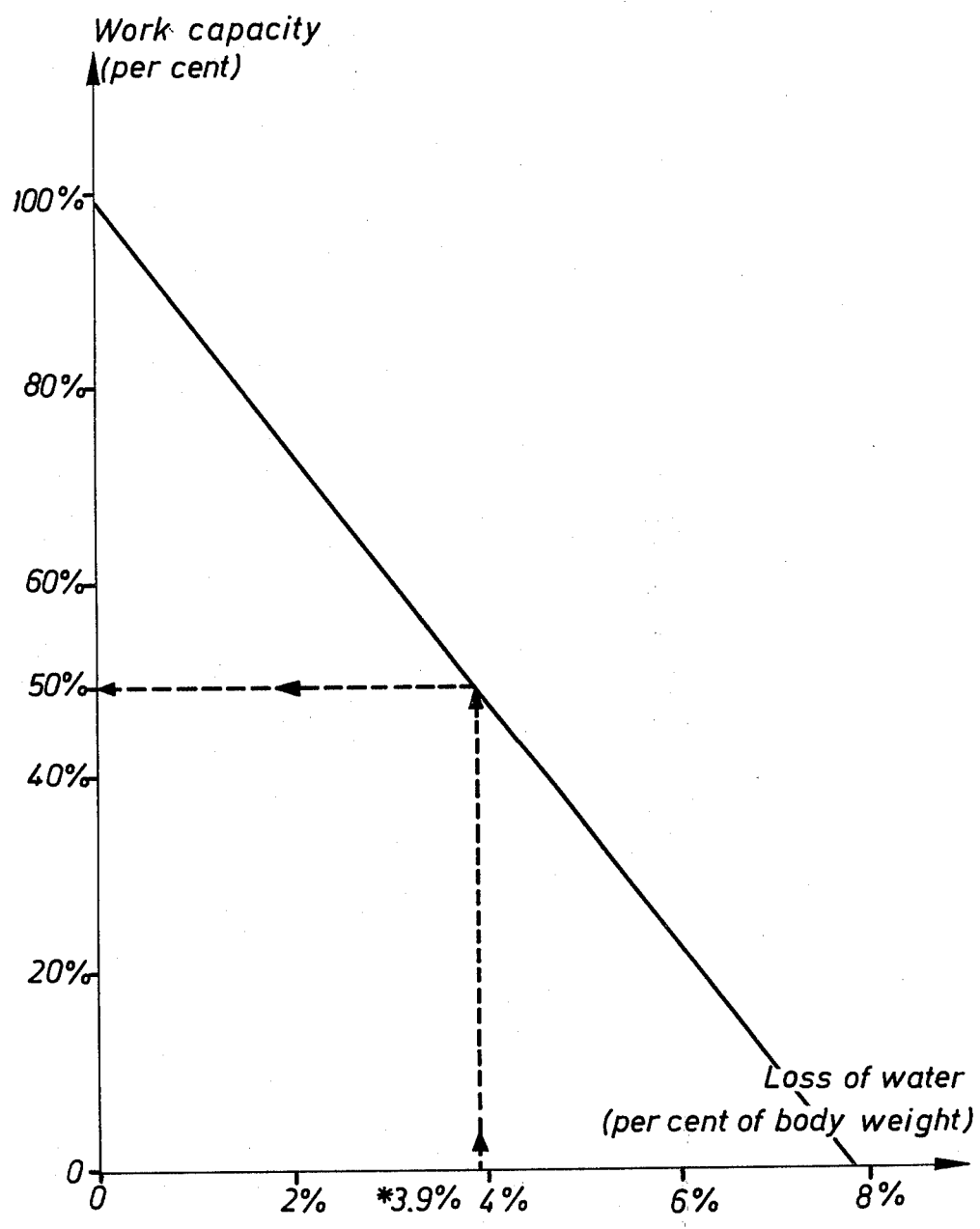

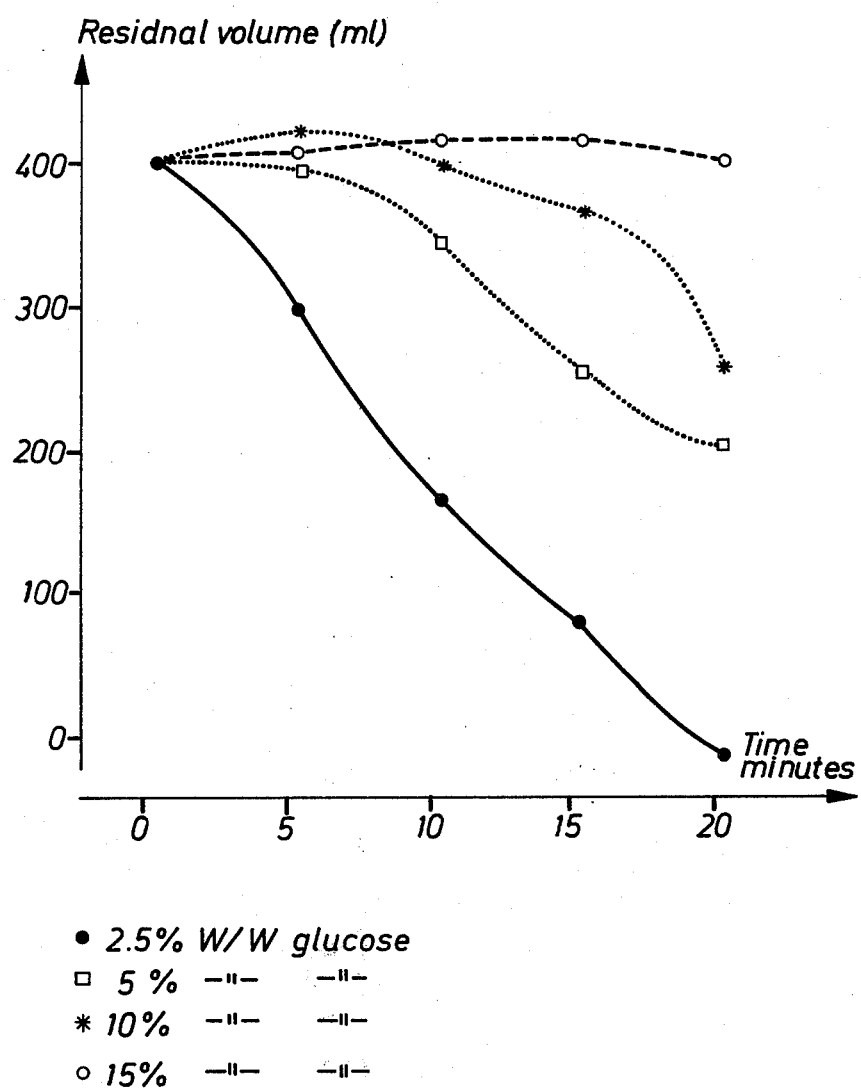

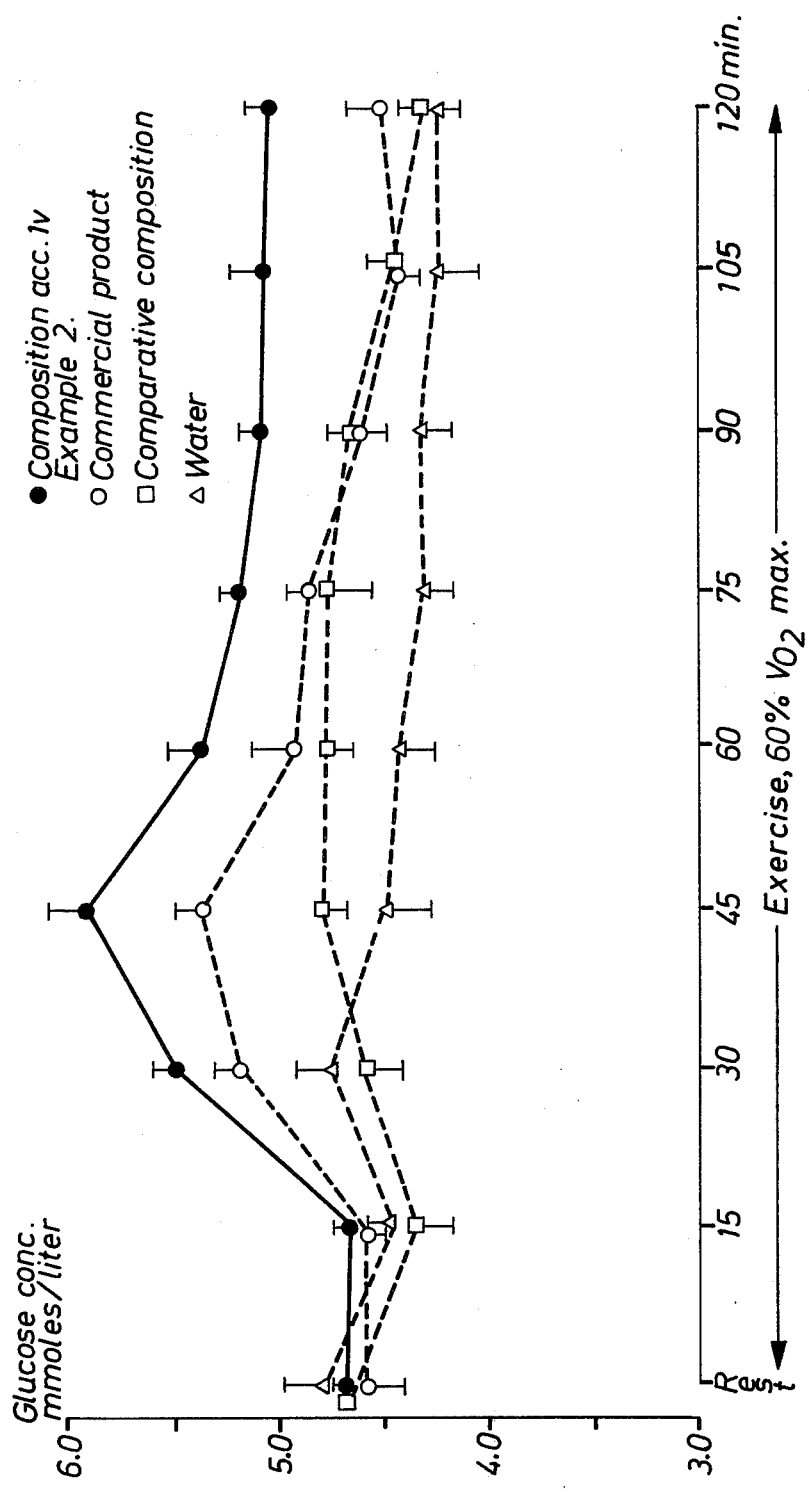

BEVERAGE PRODUCT

The present invention relates to a beverage product which is especially suitable for rapid administration of liquid and carbohydrates to the human body during periods of heavy muscle work. The invention also comprises a process for preparing the said beverage product and a process for replacing water lost by perspiration and for preventing a decrease of the glucose content of blood during periods of heavy muscle work.

During periods of relatively extended heavy work it is primarily two factors which delimit the work capacity of an individual. These are partly a low blood sugar concentration and partly loss of liquid by perspiration. The blood sugar content decreases during the work, whereas the carbohydrate reserves in liver and muscles are relatively small and all forms of muscle work cause a greatly increased glucose consumption. The losses of liquid and electrolytes by perspiration can be considerable and they depend primarily on the intensity of the work and the ambient temperature.

It is known that administration of carbohydrate-containing aqueous solutions during work causes an increased blood sugar concentration, increased insulin level and a readjustment of the metabolism of the liver in a glycogen-saving direction. After consumption of such solutions they will immediately enter the ventricle. However, in the ventricle no absorption of water or carbohydrates occurs. Such absorption occurs only after the passage of the solution through the pylorus into the intestines. The ventricular emptying rate into the intestines is an essential delimiting factor for maximal liquid administration during work. The pylorus is normally closed and its opening is essentially controlled by the osmotic pressure of the ventricular contents. Generally speaking, the lower the osmotic pressure of the contents of the ventricle the more rapid the contents is transported to the intestines. The purpose of the present invention is especially to achieve a good-tasting beverage product which has a required content of blood sugar-increasing carbohydrates but with a hypotonic osmotic pressure of such a magnitude that the consumed beverage product rapidly will pass the ventricle and enter the intestines for absorption of liquid as well as glucose formed by digested oligosaccharides and polysaccharides.

A number of different so-called sport beverages are presently marketed, which are intended to replace the liquid losses by perspiration and glucose in blood and muscles consumed are muscular efforts. The osmotic pressure in such known beverages are, however, at the most isotonic with the osmotic pressure of blood and the passage from ventricle to the intestines will thus not be optimal. This is due to the fact that such known beverages as the carbohydrate source essentially contain simple sugars such as glucose or fructose.

A beverage product according to the invention is in contrast thereto essentially monosaccharide-free and is a hypotonic solution of soluble oligosaccharides and/or polysaccharides. The simple sugars glucose and fructose have a considerably lower molecular weight than the soluble oligosaccharides and the insoluble polysaccharides. However, it has been found that the soluble oligosaccharides as well as the insoluble polysaccharides very rapidly are digested in the ventricle and intestines to the formation of resorbable monosaccharides, above all glucose. Since the simple sugars have considerably lower molecular weights than the oligosaccharides in question the solution and/or suspension thereof has a proportionally lower osmotic pressure. It is, however, desirable that the beverage product has an agreeable taste and for that purpose it is suitable that a certain level of sweetly tasting oligosaccharides is maintained in the product. It is preferred that the total amount of carbohydrates in the beverage product according to the invention is within the range 2–20% by weight.

The ready-to-consume beverage product according to the invention shall have a hypotonic osmotic pressure, preferably in the range about 7.5–1.0 atmospheres at 25° C., preferably 6.0–2.5 and especially 5.5–3.0 atmospheres. The isotonic pressure is about 7.9 atmospheres at 25° C.

Above the said carbohydrates the beverage product according to the invention suitably contains mineral salts such as sodium chloride and other salts commonly occurring in body fluids such as potassium chloride and sodium and/or potassium phosphate. During heavy body work, especially at high ambient temperatures, the body strives to decrease an increased body temperature by perspiration. The perspired liquid is a hypotonic solution containing essentially the above-mentioned salts. During relatively short periods of work it is, however, not necessary from a physiological point of view to replace salts lost by perspiration since said losses are regained in subsequent meals. However, from the point of view of taste it may be desirable that a good-tasting beverage contains a certain amount of salt. The beverage product according to the invention thus contains preferably salts of the above-mentioned kind in an amount of at the most 3 grams per liter beverage, preferably at the most 1.5 grams per liter. The beverage product suitably also contains a minor amount of aroma substances conventionally used in such products. For reasons of taste the beverage product according to the invention suitably contains one or more sweetly tasting oligosaccharides within the DP range 2–5, such as saccharose and maltotriose, in combination with polysaccharides with an average molecular weight in the range from 900 up to the molecular weight of starch. A preferred form of the beverage product according to the invention, which is essentially clearly water-soluble, contains a, from the taste point of view, desirable content of one or more sweetly tasting oligosaccharides within the DP range 2–5 such as saccharose and maltotriose, in combination with polysaccharides with a molecular weight in the range of about 900–2500.

Another preferred beverage product according to the invention is characterized in that it per liter ready-to-consume beverage contains 20–70 grams of saccharose, 5–200 grams of other essentially water-soluble oligosaccharides with an average molecular weight in the range of about 900–2500 and mineral salts in an amount of about 0.5–1.5 grams per liter beverage and, if desired, aroma substances and vitamins.

A specific form of the above-defined beverage product according to the invention, which is especially adapted for use at ambient temperatures below 0° C., is characterized in that the content of soluble oligosaccharides is within the upper part of the above-mentioned range, e.g. 100–200 grams per liter, and the content of saccharose is within the lower part of the range, e.g. 20–55 grams per liter beverage, its osmotic pressure being within the range 7.5–4.5 atmospheres, especially 5.0–6.0 atmospheres. This specific form of the beverage product has thus a relatively high content of carbohydrates in relation to the water content since during periods of body work at low temperatures such as below 0° C. the liquid losses by perspiration are relatively low whereas the glucose consumption is very great.

A second specific form of the beverage product which is especially adapted for use in ambient temperatures above 25° C. is characterized in that the content of soluble oligosaccharides is within the lower part of the said range, e.g. 0.5–1.5 grams per liter, and the content of saccharose is likewise within the lower part of the said range, e.g. 20–40 grams per liter, calculated on the ready-to-consume beverage, its osmotic pressure being within the range 1.0–4.5 atmospheres, especially 2.5–4.0 atmospheres.

The invention also comprises a process for preparing the beverage product according to the invention, which process is characterized in that essentially monosaccharide-free and water-soluble oligosaccharides and optionally water-insoluble polysaccharides and a minor amount of up to about 3.0 grams per liter of the finished beverage of soluble mineral salts occurring in body liquids, such as sodium chloride, preferably also conventional soluble aroma substances, are dissolved and/or dispersed in water in such an amount that the finished solution or suspension has a hypotonic osmotic pressure within the range about 7.5–1.0 atmospheres at 25° C., preferably 6.0–2.5, and most preferred 5.5–3.0 atmospheres.

The invention also comprises a process for rapidly replacing water lost by perspiration and for preventing a decrease of the glucose content of blood during periods of heavy muscle work, which is characterized in that the body per os is administrated a beverage product of the above-defined type.

The expression "essentially monosaccharide-free" in the definition of the oligosaccharides and/or polysaccharides present in the beverage product according to the invention is intended to mean that a minor amount of monosaccharide can be present therein due to the preparation process of the saccharides. A minor amount of monosaccharide which may be present due to the preparation process is, however, not desirable and should be kept as low as practically possible. Commercially available oligosaccharide products with a molecular weight range up to about 2500 commonly contain a few percent by weight of glucose which can be tolerated for the most purposes.

Extensive practical experiments have been performed for the purpose of studying the change of blood sugar concentration during work in connection with administration of solutions with varying carbohydrate concentrations. Healthy individuals have been submitted to testing in connection with extensive heavy work on an ergometer bicycle and the glucose and lactate concentrations in venous blood have been determined at regular intervals.

In a representative experiment 8 healthy volunteers participated (6 males, 2 women, in the age range of 17–46 years) who were experienced in bicycle racing. The maximial oxygen uptake of the participants was in average 4.1 liters per minute (the range was 2.8–5.3 liters per minute). The participants were checked at four different times. Each time blood samples were collected from venous blood from the elbow for analysis of the glucose and lactate concentrations at rest and at repeated times during work on a bicycle ergometer (2 hours, 60% of maximal aerobic capacity). During the work periods the participants were given 1000 mls/hour of four different test beverages, subdivided in four portions of 250 mls each 15th minute. The four test solutions had the following compositions per liter beverage:

| (1) | Product according to Example 2 below. | |
|---|---|---|
| | Saccharose | 65 grams |
| | Oligosaccharide with a molecular weight within the range above 300–2000 | 15 grams |
| | Citric acid | 1.8 grams |
| | Mineral salts | 1 gram |
| (2) | Commercial product. | |
| | Glucose | 35 grams |
| | Fructose | 20 grams |
| | Mineral salts | 1.6 grams |
| (3) | Comparative product with the same osmotic pressure as the product according to Example 2. | |
| | Glucose | 12.5 grams |
| | Fructose | 22 grams |
| | Mineral salts | 1 gram |
| (4) | Water. | |

All 8 participants participated in work during administration as mentioned above of beverages (1), (2) and (4), whereas 5 persons were present in the group administrated solution (3).

The work was conducted on a bicycle ergometer of the type "Siemens Elema". The pulse frequency during rest and during work was determined by EKG.

The glucose and lactate concentrations in venous blood were analyzed enzymatically. The maximal oxygen uptake for the participants was determined in a separate investigation, the work on a bicycle ergometer being stepwise increased and the aspirated air was collected in Douglas bags. The oxygen and carbon dioxide contents therein were analyzed according to Scholander.

During the said experiments the participants worked during two hours at a work load corresponding to 60% of the maximal oxygen uptake capacity.

The results are shown in FIG. 3.

The blood sugar content before the work period was $4.7 \pm 0.2$ mmoles/liter which indicated that the participants were in a basal metabolic condition. During work and administration of solution (1) the glucose concentration initially increased and reached its highest value ($+28 \pm 5\%$) about 45 minutes after the start of the work (cf. Table I and FIG. 1). Thereafter the glucose content decreased and reached a plateau value which was about 5–10% higher than the concentration during rest before work. This level was maintained until the end of the work period.

Similar concentration changes were observed when the participants were administrated the commercial product (solution 2). Initially there was a peak after 45 minutes ($+18 \pm 5\%$) and then the glucose content successively decreased and after two hours it reached the initial value. However, at all determination times the blood sugar concentration was significantly lower when the commercial product was administrated as compared to the product according to Example 2 (FIG. 1). During administration of solution (3) there was no initial increase of the blood sugar content. However, the said content was essentially unchanged up to 90 minutes, when a slow decrease could be noticed ($-10 \pm 4\%$ at the end of the work).

The control study with water (solution 4) gave significantly lower blood sugar concentration than in the other groups. At the end of the work there was, however, no significant difference as regards the glucose concentration for the administration of water, solution (3) or the commercial product (solution 2). Only when the participants were administrated the product according to Example 2 a blood sugar content which was higher than the one for water administration (+18%) was obtained.

The lactate concentration in venous blood during rest conditions was 0.8+0.1 mmole/liter. In all of the groups there was a small initial increase of the lactate content (+10-20%), whereafter the concentration decreased to the initial value (cf. Table II). There were no differences in the lactate contents during work in connection with administration of the different beverages (cf. Table II).

The pulse frequency during work increased during the first minutes to about 140-150 beats/minute and during the continued work there was a small further increase of the pulses frequency of about 10%. The pulse frequency was the same after administration of all experimental beverages.

The results obtained show that administration of the product according to Example 2 of the invention in connection with extended heavy work results in a higher blood sugar concentration as compared with the cases after administration of the commercial product (solution 2), solution (3) and water. The higher glucose content after administration of the product according to Example 2 gives an improved substrate distribution in the working muscles and this seems to indicate that glycogen present in the muscles and in the liver can be saved. The ability of extended work is generally delimited by a decreasing blood sugar content which results in muscular exhaustion and decrease of the brain function. The experiments seem to indicate that this can be prevented by administration of the product according to Example 2 during work. The work capacity during extended periods can thus be improved.

The results seem to indicate that the resorption in the intestines of the carbohydrates in the product according to Example 2 were more rapid as compared to the resorption of the other products. This is probably due to the fact that the product according to the invention is essentially free from monosaccharides. For this reason the osmotic pressure of the solution will be lower than for the solutions which mainly contains monosaccharides. As mentioned above the emptying rate of the ventricle is largely dependent on the osmotic pressure of the content of the ventricle. Further, the emptying of the ventricle rather than the resorption of the carbohydrates from the intestines is delimiting for the amount of liquid and carbohydrates which can be used during work. The above-mentioned experiments thus seem to indicate that the lower hypotonic osmotic pressure in the product according to the invention in comparison with the commercial product caused a more rapid passage of the beverage through the ventricle out into the intestines, wherein the administrated carbohydrates rapidly were digested to monosaccharide so that the high blood sugar content during work could be maintained. This is also indicated by the results obtained with beverage No. 3. This beverage contained carbohydrates in the form of the monosaccharides glucose and fructose in such an amount (34.5 grams/liter) that the osmotic pressure of the solution was the same as in the product according to Example 2. These two solutions should thus have passed the ventricle with the same speed. The lower blood sugar content after administration of solution (3) is obviously due to the lower carbohydrate content therein in comparison with the product according to Example 2.

The pulse frequency and the lactate concentration in blood were the same for the different beverages which shows that the circulatory adaptation was similar in all groups. The higher glucose content in the blood after consumption of the product according to Example 2 is thus not caused by a hemo concentration during work.

The conclusion of the experiments performed is that administration of a product according to the invention during an extended period of heavy work contributes to the maintenance of a high blood sugar concentration and an improved capacity for long time work. The experiments also show that the favourable effect of the product according to the invention as compared with the effect of the other tested beverages depends on its low hypotonic osmotic pressure in relation to the carbohydrate content.

TABLE I.

Glucose and lactate concentration in venous blood before and during work on a bicycle ergometer (60% of maximal aerobic capacity) during administration of different beverages.

| | Rest | 15 | 30 | 45 | Work 60 | 75 | 90 | 105 | 120 minutes |
|---|---|---|---|---|---|---|---|---|---|
| Glucose concentration mmole/liter | | | | | | | | | |
| Product according to Example 2 | 4.63 ± 0.10 | 4.65 ± 0.06 | 5.49 ± 0.08 | 5.90 ± 0.18 | 5.36 ± 0.16 | 5.18 ± 0.09 | 5.06 ± 0.08 | 5.04 ± 0.18 | 5.02 ± 0.12 |
| Commercial product | 4.60 ± 0.20 | 4.59 ± 0.11 | 5.21 ± 0.08 | 5.37 ± 0.09 | 4.91 ± 0.11 | 4.85 ± 0.11 | 4.61 ± 0.15 | 4.40 ± 0.16 | 4.49 ± 0.17 |
| Comparative product | 4.71 ± 0.08 | 4.34 ± 0.19 | 4.61 ± 0.20 | 4.79 ± 0.13 | 4.78 ± 0.16 | 4.75 ± 0.23 | 4.67 ± 0.20 | 4.42 ± 0.11 | 4.29 ± 0.12 |
| Water | 4.70 ± 0.21 | 4.45 ± 0.14 | 4.75 ± 0.19 | 4.49 ± 0.23 | 4.42 ± 0.19 | 4.31 ± 0.14 | 4.32 ± 0.15 | 4.22 ± 0.19 | 4.27 ± 0.15 |
| Lactate concentration mmole/liter | | | | | | | | | |
| Product according to Example 2 | 0.80 ± 0.10 | 1.07 ± 0.24 | 1.01 ± 0.20 | 1.04 ± 0.18 | 0.98 ± 0.14 | 0.94 ± 0.12 | 0.95 ± 0.13 | 0.97 ± 0.15 | 0.94 ± 0.13 |
| Commercial product | 0.83 ± 0.07 | 0.99 ± 0.20 | 0.92 ± 0.18 | 0.90 ± 0.16 | 0.87 ± 0.16 | 0.88 ± 0.17 | 0.83 ± 0.14 | 0.88 ± 0.13 | 0.83 ± 0.13 |
| Comparative product | 0.82 ± 0.06 | 1.21 ± 0.26 | 1.02 ± 0.25 | 1.01 ± 0.23 | 1.01 ± 0.25 | 1.00 ± 0.24 | 0.95 ± 0.21 | 1.00 ± 0.19 | 0.93 ± 0.27 |

TABLE I.-continued

Glucose and lactate concentration in venous blood before and during work on a bicycle ergometer (60% of maximal aerobic capacity) during administration of different beverages.

| | Rest | \-\-\-\-\-\-\-\-\-\-\-\-\-\-\-\-\-\-\-\-\-\-\-\-\-\-\-\-\-\-\-\-\-\-\-\-\-\-\- Work \-\-\-\-\-\-\-\-\-\-\-\-\-\-\-\-\-\-\-\-\-\-\-\-\-\-\-\-\-\-\-\-\-\-\-\-\-\-\- | | | | | | | 120 |
|---|---|---|---|---|---|---|---|---|---|
| | | 15 | 30 | 45 | 60 | 75 | 90 | 105 | minutes |
| Water | 0.77 ± 0.10 | 1.08 ± 0.28 | 0.99 ± 0.24 | 0.89 ± 0.18 | 0.81 ± 0.18 | 0.84 ± 0.16 | 0.72 ± 0.12 | 0.79 ± 0.12 | 0.83 ± 0.12 |

TABLE II.

Pulse frequency during work (60% of maximal aerobic capacity) in connection with administration of beverages.

| | \-\-\-\-\-\-\-\-\-\-\-\-\-\-\-\-\-\-\-\-\-\-\-\-\-\-\-\-\-\-\-\-\- Work \-\-\-\-\-\-\-\-\-\-\-\-\-\-\-\-\-\-\-\-\-\-\-\-\-\-\-\-\-\-\-\-\- | | | | | |
|---|---|---|---|---|---|---|
| | 20 min. | 40 min. | 60 min. | 80 min. | 100 min. | 120 min. |
| Product according to Example 2 | 142 ± 7 | 146 ± 7 | 147 ± 7 | 149 ± 7 | 149 ± 7 | 154 ± 6 |
| Commercial product | 140 ± 6 | 144 ± 7 | 146 ± 7 | 147 ± 7 | 138 ± 4 | 149 ± 6 |
| Comparative product | 146 ± 11 | 148 ± 12 | 152 ± 12 | 155 ± 12 | 158 ± 12 | 158 ± 12 |
| Water | 144 ± 7 | 145 ± 8 | 145 ± 8 | 145 ± 8 | 148 ± 9 | 148 ± 8 |

The invention is elucidated by the following non-delimiting examples.

EXAMPLE 1

General purpose sport beverage

| | grams/liter beverage |
|---|---|
| Saccharose | 55 |
| Oligosaccharides* | 20 |
| Citric acid | 1.8 |
| Citric aroma | 1.0 |
| NaCl | 1.0 |

*A commercial mixture of essentially water-soluble oligosaccharides with an average molecular weight in the range about 1740–2100.

The components were mixed in the dry state and dissolved in 1 liter of water. A sport beverage with an agreeable taste was obtained which had an osmotic pressure of about 5.0 atmospheres at 25° C.

EXAMPLE 2

General purpose sport beverage

| | grams/liter beverage |
|---|---|
| Saccharose | 60 |
| Oligosaccharides* | 15 |
| Citric acid | 1.8 |
| Citric aroma | 1.0 |
| NaCl | 0.6 |
| KCl | 0.1 |
| NaH$_2$PO$_4$ | 0.1 |
| K$_2$HPO$_4$ | 0.1 |
| NaHCO$_3$ | 0.1 |

*A commercial mixture of essentially water-soluble oligosaccharides with an average molecular weight in the range about 900–1050.

Dry mixture and dissolution of the components in 1 liter of water gave a good-tasting beverage with an osmotic pressure of 5.4 atmospheres at 25° C.

EXAMPLE 3

Sport beverage especially adapted for temperatures above 25° C.

| | grams/liter beverage |
|---|---|
| Saccharose | 30 |
| Oligosaccharides* | 10 |
| Citric acid | 0.8 |
| Citric aroma | 1.0 |
| NaCl | 0.6 |
| KCl | 0.1 |
| NaH$_2$PO$_4$ | 0.1 |
| K$_2$HPO$_4$ | 0.1 |
| NaHCO$_3$ | 0.1 |

*A commercial mixture of essentially water-soluble oligosaccharides with an average molecular weight in the range about 900–1050.

Dry-mixing of the components and dissolution in 1 liter of water gave a good-tasting sport beverage with an osmotic pressuure of about 3.5 atmospheres at 25° C. The especially low hypotonic osmotic pressure and the relatively low saccharide content made the beverage especially suitable for use at high ambient temperatures above 25° C. when administration of liquid is especially important.

EXAMPLE 4

Sport beverage especially adapted for use at low ambient temperatures below 0° C.

| | grams/liter beverage |
|---|---|
| Saccharose | 45 |
| Oligosaccharides* | 105 |
| Citric acid | 1.8 |
| Citric aroma | 1.0 |
| NaCl | 0.6 |
| KCl | 0.1 |
| NaH$_2$PO$_4$ | 0.1 |
| K$_2$HPO$_4$ | 0.1 |
| NaHCO$_3$ | 0.1 |

*A commercial mixture of essentially water-soluble oligosaccharides with an average molecular weight in the range about 900–1050.

Dry-mixing of the components and dissolution in 1 liter of water gave a good-tasting sport beverage with an osmotic pressure of 5.2 atmospheres at 25° C. The relatively high content of saccharides made the beverage especially suitable for use at relatively low temperatures below 0° C. when carbohydrate administration is especially important.

EXAMPLE 5

Dry powderous product suitable as spare provisions

|  | grams/liter beverage |
|---|---|
| Saccharose | 20 |
| Oligosaccharides* | 105 |
| Starch meal | 95 |
| Aroma substances (dry) | 3 |
| Sodium chloride | 1 |
| Vitamin mix | 1 |

*A commercial mixture of essentially water-soluble oligosaccharides with an average molecular weight in the range about 900-1050.

Dry-mixng of the components and packing in hermetically sealed bags gave a product suitable as spare provisions for emergency situations. Before use the powder is dispersed in water and consumed in a hot or cold condition. The low osmotic pressure (3.6 atmospheres at 25° C.) at recommended addition of water ensures a rapid passage through the ventricle out into the intestines which results in a rapid increase of the blood sugar content.

In the enclosed drawings FIG. 1 shows the work capacity as a function of the liquid loss during heavy muscle work; in FIG. 2 the emptying rate of the ventricle is shown after consumption of glucose solutions with different concentrations; and FIG. 3 shows the glucose content of blood during heavy muscle work and with administration of different test beverages at regular intervals.

As can be seen from FIG. 1 the work capacity decreases rapidly with the loss of body liquids by perspiration. It is remarkable that a loss of 3.9% of liquid, calculated on the body weight, causes an about 50% loss of the work capacity. This indicates the importance of replacing liquid lost during work.

In the experiments elucidated in FIG. 2 persons parttaking in the experiments were given glucose solutions in water with the concentrations 2.5%, 5%, 10% and 15%, calculated on the weight. Equal volumes of each solution were consumed. The diagram shows that a glucose solution with the concentration 2.5% after 20 minutes had passed the ventricle completely, whereas a 15% glucose solution remains in the ventricle after the same period of time. The solutions with intermediary glucose concentrations 5 and 10% had intermediary values.

We claim:

1. Beverage product, especially for rapid replacement of liquid and carbohydrates in the human body during periods of extended heavy muscle work, characterized in that it consists of an essentially monosaccharide-free, hypotonic solution of soluble oligosaccharides having a degree of polymerization (DP) of up to 10 and/or polysaccharides and mineral salts selected from the group consisting of sodium chloride, potassium chloride, sodium bicarbonate, sodium dihydrogen phosphate and potassium hydrogen phosphate, in an amount of at the most 3 grams per liter beverage, which solution may contain suspended particles of insoluble polysaccharides, optionally also a minor amount of aroma substances conventionally used in such beverages.

2. Beverage product according to claim 1, characterized in that the solution or the suspension has an osmotic pressure in the range about 7.5-1.0 atmospheres at 25° C., preferably 6.0-2.5 and especially 5.5-3.0 atmospheres.

3. Beverage product according to claim 1 or 2, characterized in that it contains, from the human taste point of view a desirable content of one or more sweetly tasting oligosaccharides in the DP range 2-5 as represented by saccharose and maltotriose, in combination with polysaccharides with an average molecular weight in the range from 900 up to the molecular weight of starch.

4. Beverage product according to claim 2, characterized in that it contains from the human taste point of view a desirable content of one or more sweetly tasting oligosaccharides within the DP range 2-5 as represented by saccharose and maltotriose, in combination with polysaccharides with a molecular weight in the range about 900-2500, in which case the product is essentially clearly water-soluble.

5. Beverage product according to claim 4, characterized in that it per liter finished beverage contains 20-70 grams of saccharose, 5-200 grams of essentially water-soluble oligosaccharides with an average molecular weight in the range about 900-2500, aroma substances and mineral salts in an amount of about 0.5-1.5 grams per liter beverage.

6. Beverage product according to claim 5, especially adapted for use at ambient temperatures below 0° C., characterized in that the content of soluble oligosaccharides is 100-220 grams per liter, and the content of saccharose is 20-55 grams per liter finished beverage, its osmotic pressure being within the range 7.5-4.5 atmospheres, especially 5.0-6.0 atmospheres at 25° C.

7. Beverage product according to claim 5, especially adapted for use at ambient temperatures above 25° C., characterized in that the content of soluble oligosaccharides is 0.5-1.5 grams per liter, and the content of saccharose likewise is 20-40 grams per liter, calculated on the finished beverage, its osmotic pressure being within the range 1.0-4.5 atmospheres, especially 2.5-4.0 atmospheres at 25° C.

8. Beverage product according to claim 1 characterized in that its total carbohydrate content is within the range 2-20% by weight.

9. Beverage product according to claim 1 characterized in that it is in the form of a suitably completely dry concentrate intended for dissolution in water.

10. A process for preparing a beverage product according to claim 1 characterized in that essentially monosaccharide-free and water-soluble oligosaccharides and optionally water-insoluble polysaccharides and a minor amount of up to about 3.0 grams per liter finished beverage, preferably up to about 1.5 grams per liter, of soluble mineral salts as defined in claim 1, preferably also conventional soluble aroma substances, are dissolved and/or dispersed in water in such an amount that the finished solution/suspension has an osmotic pressure in the range about 7.5-1.0 atmospheres at 25° C., preferably 6.0-2.5 atmospheres, especially 5.5-3.0 atmospheres.

11. A process for rapidly replacing water lost by perspiration and preventing a decrease of the glucose content of blood during periods of heavy muscle work by a human, characterized by per os administering of a beverage product, to said human, as defined in claim 1.

* * * * *